(12) United States Patent
Motyka et al.

(10) Patent No.: US 7,838,042 B2
(45) Date of Patent: *Nov. 23, 2010

(54) HYPOALLERGENIC METAL AMINO ACID CHELATES AND METAL AMINO ACID CHELATE-CONTAINING COMPOSITIONS

(75) Inventors: Max R. Motyka, St. Clair Shores, MI (US); Rick Harnish, Miami, FL (US); Stephen D. Ashmead, Clinton, UT (US); H. DeWayne Ashmead, Fruit Heights, UT (US)

(73) Assignee: Albion International, Inc., Clearfield, UT (US)

( * ) Notice: Subject to any disclaimer, the term of this patent is extended or adjusted under 35 U.S.C. 154(b) by 1136 days.

This patent is subject to a terminal disclaimer.

(21) Appl. No.: 10/828,827

(22) Filed: Apr. 21, 2004

(65) Prior Publication Data

US 2005/0239750 A1 Oct. 27, 2005

(51) Int. Cl.
*A61K 33/00* (2006.01)
*A61K 33/26* (2006.01)
*A61K 33/30* (2006.01)
*A61K 33/32* (2006.01)
*A61K 33/34* (2006.01)
*A01N 59/00* (2006.01)
*A01N 59/16* (2006.01)
*A01N 59/20* (2006.01)

(52) U.S. Cl. ............. 424/600; 424/638; 424/639; 424/643; 424/647

(58) Field of Classification Search ............. 424/618, 424/630, 639, 641, 646, 647, 648, 655, 682; 514/492, 494, 499, 502, 505, 836
See application file for complete search history.

(56) References Cited

U.S. PATENT DOCUMENTS

| | | | |
|---|---|---|---|
| 3,969,540 A | 7/1976 | Jensen | |
| 4,020,158 A | 4/1977 | Ashmead et al. | |
| 4,076,803 A | 2/1978 | Ashmead | |
| 4,103,003 A | 7/1978 | Ashmead | |
| 4,167,564 A | 9/1979 | Jensen | |
| 4,169,716 A | 10/1979 | Ashmead | |
| 4,169,717 A | 10/1979 | Ashmead | |
| 4,172,072 A | 10/1979 | Ashmead | |
| 4,201,793 A | 5/1980 | Ashmead | |
| 4,216,143 A | 8/1980 | Ashmead | |
| 4,216,144 A | 8/1980 | Ashmead | |
| 4,491,464 A | 1/1985 | Ashmead et al. | |
| 4,529,434 A | 7/1985 | Ashmead | |
| 4,599,152 A | 7/1986 | Ashmead | |
| 4,725,427 A * | 2/1988 | Ashmead et al. | 424/44 |
| 4,774,089 A | 9/1988 | Ashmead | |
| 4,830,716 A | 5/1989 | Ashmead | |
| 4,863,898 A | 9/1989 | Ashmead et al. | |
| 5,162,369 A | 11/1992 | Ashmead et al. | |
| 5,270,297 A | 12/1993 | Paul et al. | |
| 5,292,538 A | 3/1994 | Paul et al. | |
| 5,292,729 A | 3/1994 | Ashmead | |
| 5,504,055 A * | 4/1996 | Hsu | 504/121 |
| 5,516,925 A | 5/1996 | Pedersen et al. | |
| 5,596,016 A | 1/1997 | Ashmead et al. | |
| 5,614,553 A | 3/1997 | Ashmead et al. | |
| 5,882,685 A | 3/1999 | Ashmead | |
| 5,888,553 A | 3/1999 | Grant et al. | |
| 6,114,379 A | 9/2000 | Wheelwright et al. | |
| 6,159,530 A | 12/2000 | Christiansen et al. | |
| 6,166,071 A | 12/2000 | Ashmead et al. | |
| 6,207,204 B1 | 3/2001 | Christiansen et al. | |
| 6,294,207 B1 | 9/2001 | Christiansen et al. | |
| 6,299,896 B1 * | 10/2001 | Cooper et al. | 424/441 |
| 6,299,914 B1 | 10/2001 | Christiansen et al. | |
| 6,407,138 B1 | 6/2002 | Ashmead et al. | |
| 6,426,424 B1 * | 7/2002 | Ashmead et al. | 556/1 |
| 6,458,981 B1 | 10/2002 | Ashmead et al. | |
| 6,518,240 B1 | 2/2003 | Pedersen et al. | |
| 6,706,904 B1 | 3/2004 | Hartle et al. | |
| 6,710,079 B1 | 3/2004 | Ashmead et al. | |
| 6,716,814 B2 | 4/2004 | Ericson et al. | |

OTHER PUBLICATIONS

Nakamoto et al. J. Am. Chem. Soc. 1961 83(22), 4528-4532.*
Lumb et al. J. Phys. Chem. 1953, 57(7), 690-693.*
Izumi et al. Angew. Chem. Int. Ed. Engl. 1978, 17, 176-183.*
Determination of Amino Acids in Cell Cultures and Fermentation Broths, Dionex Application Note 150, pp. 1-15.
Riccardi, Giovanna et al., Production of Amino Acids by Analog-Resistant Mutants of Cyanobacterium *Spirulina platenis*, Journal of Bacteriology, (Sep. 1981), pp. 1002-1007.

(Continued)

*Primary Examiner*—Ernst V Arnold
(74) *Attorney, Agent, or Firm*—Thorpe North & Western LLP

(57) ABSTRACT

Hypoallergenic metal amino acid chelate compositions, hypoallergenic formulations containing hypoallergenic metal amino acid chelates, methods of preparing hypoallergenic metal amino acid chelate, and methods of administering hypoallergenic metal amino acid chelates are provided. Specifically, the present invention provides metal amino acid chelates that are substantially free of allergens such that administration of the metal amino acid chelates to a subject in an effective amount to cause a medicinal or nutritional result does not produce a discernable adverse allergic reaction. The metal amino acid chelates can include chelates having a naturally occurring amino acid to metal molar ratio of from about 1:1 to 4:1.

55 Claims, No Drawings

OTHER PUBLICATIONS

Cattle Nutrition—Mycotoxins and Intoxications, Abstracts—XXII World Buiatrics Congress 2002, (Aug. 18-23, 2002—Abstract Nos. 1-364, 2-689, 3-229, 4-788, 5-755, 6-157, 7-825, 7-757, 9-226, 10-393, 11-645, 12-904, 13-802), Hannover, Germany.

Toride, Yasuhiko, Lysine and other amino acids for feed: production and contribution to protein utilization in animal feeding.

Takahashi, N. et al., Acid-neutralizing activity during amino acid fermentation by *Porphyromonas gingivalis, Prevotell intermedia* and *Fusobacterium nucleatum*, Oral Microbiology Immunology, (Apr. 2003), 109-113(5), vol. 18, No. 2.

Amino Acides are Made from Natural Materials, Encyclopedia of Amino Acids, Apr. 9, 2004, pp. 1-2.

Lumb, R.F. et al., "Metal Chelating Tendencies of Glutamic and Aspartic Acids," J. Phys. Chem. 1953, vol. 57, No. 7, pp. 690-693.

Nakamoto, Kazuo, et al., "Infrared Spectra of Aqueous Solutions. I. Metal Chelate Compounds of Amino Acids," J. Am. Chem. Soc., 1961, vol. 83, No. 22, pp. 4528-4532.

Determination of Amino Acids in Cell Cultures and Fermentation Broths, Dionex Application Note 150, pp. 1-15, 2003.

\* cited by examiner

HYPOALLERGENIC METAL AMINO ACID CHELATES AND METAL AMINO ACID CHELATE-CONTAINING COMPOSITIONS

FIELD OF THE INVENTION

The present invention is drawn to hypoallergenic metal amino acid chelates and hypoallergenic formulations containing hypoallergenic metal amino acid chelates.

BACKGROUND OF THE INVENTION

Amino acid chelates are generally produced by the reaction between α-amino acids and metal ions having a valence of two or more to form a ring structure. In such a reaction, the positive electrical charge of the metal ion can be neutralized by the electrons available through the carboxylate or free amino groups of the α-amino acid.

Traditionally, the term "chelate" has been loosely defined as a combination of a polyvalent metallic ion bonded to one or more ligands to form a heterocyclic ring structure. Under this definition, chelate formation through neutralization of the positive charge(s) of the metal ion may be through the formation of ionic, covalent, or coordinate covalent bonding. An alternative and more modern definition of the term "chelate" requires that the polyvalent metal ion be bonded to the ligand solely by coordinate covalent bonds forming a heterocyclic ring. In either case, both are definitions that describe a metal ion and a ligand forming a heterocyclic ring.

Chelation can be confirmed and differentiated from mixtures of components by infrared spectra through comparison of the stretching of bonds or shifting of absorption caused by bond formation. As applied in the field of mineral nutrition, there are certain "chelated" products that are commercially utilized. One product is referred to as an "amino acid chelate." When properly formed, an amino acid chelate is a stable product having one or more five-membered rings formed by a reaction between the amino acid and the metal. The American Association of Feed Control Officials (AAFCO) has also issued a definition for amino acid chelates. It is officially defined as the product resulting from the reaction of a metal ion from a soluble metal salt with amino acids having a mole ratio of one mole of metal to one to three (preferably two) moles of amino acids to form coordinate covalent bonds. The products are identified by the specific metal forming the chelate, e.g., iron amino acid chelate, copper amino acid chelate, etc.

In further detail with respect to amino acid chelates, the carboxyloxygen and the α-amino group of the amino acid each bond with the metal ion. Such a five-membered ring is defined by the metal atom, the carboxyloxygen, the carbonyl carbon, the α-carbon, and the α-amino nitrogen. The actual structure will depend upon the ligand to metal mole ratio and whether the carboxyloxygen forms a coordinate covalent bond or a more ionic bond with the metal ion. Generally, the amino acid to metal molar ratio is at least 1:1 and is preferably 2:1 or 3:1. However, in certain instances, the ratio can be 4:1. Most typically, an amino acid chelate with a divalent metal can be represented at a ligand to metal molar ratio of 2:1 according to Formula 1 as follows:

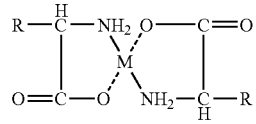

Formula 1

In the above formula, the dashed lines represent coordinate covalent bonds, covalent bonds, or ionic bonds. Further, when R is H, the amino acid is glycine, which is the simplest of the α-amino acids. However, R could be representative of any other side chain that, when taken in combination with the rest of the amino acid structure(s), results in any of the other twenty or so naturally occurring amino acids that are typically derived from proteins. All of the amino acids have the same configuration for the positioning of the carboxyloxygen and the α-amino nitrogen with respect to the metal ion. In other words, the chelate ring is defined by the same atoms in each instance, even though the R side chain group may vary.

The reason a metal atom can accept bonds over and above the oxidation state of the metal is due to the nature of chelation. For example, at the α-amino group of an amino acid, the nitrogen contributes to both of the electrons used in the bonding. These electrons fill available spaces in the d-orbitals forming a coordinate covalent bond. Thus, a metal ion with a normal valency of +2 can be bonded by four bonds when fully chelated. In this state, the chelate is completely satisfied by the bonding electrons and the charge on the metal atom (as well as on the overall molecule) can be zero. As stated previously, it is possible that the metal ion can be bonded to the carboxyloxygen by either coordinate covalent bonds or more ionic bonds.

The structure, chemistry, bioavailability, and various applications of amino acid chelates are well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,725,427; 4,774,089; 4,830,716; 4,863,898; 5,292,538; 5,292,729; 5,516,925; 5,596,016; 5,882,685; 6,159,530; 6,166,071; 6,207,204; 6,294,207; 6,458,981, 6,518,240, 6,614,553; each of which is incorporated herein by reference.

One advantage of amino acid chelates in the field of mineral nutrition is attributed to the fact that these chelates are readily absorbed from the gut and into mucosal cells by means of active transport. In other words, the minerals can be absorbed along with the amino acids as a single unit utilizing the amino acids as carrier molecules. Therefore, the problems associated with the competition of ions for intestinal absorption sites and the suppression of specific nutritive mineral elements by others can be avoided.

Many persons suffer from various allergies, which can be caused by ingesting food, liquids, or supplements containing allergens. Although the biochemistry of allergic reactions is not precisely understood, it is believed that the allergens cause, upon ingestion or other contact with the body, a specific reagin to be formed in the bloodstream. A response to an allergen by some is thought to be an inherited characteristic. In a person that is allergic to a specific allergen, the allergen, which is often a protein, can be regarded as a key which fits the corresponding structural shape of the reagin molecule.

Allergic reactions can result in symptoms ranging from very mild to very severe, some of which can cause death. For example, symptoms, both mild and severe, include skin rashes (allergic eczema and urticaria), dermal symptoms, respiratory symptoms (including allergic rhinitis and bronchial asthma), gastrointestinal symptoms, and migraine headaches. Violent illnesses have been known to include shock-like reactions, vascular collapse, and allergic anaphylaxis.

As amino acids used to prepare amino acid chelates are typically derived from protein hydrolysis, such amino acids can cause allergic reactions in a small percentage of the population. As a result, it would be an advancement in the art to provide hypoallergenic amino acid chelates and hypoallergenic formulations that contain amino acid chelates in order to avoid undesired allergic reactions.

SUMMARY OF THE INVENTION

It has been recognized that the preparation and/or administration of hypoallergenic chelates and formulations containing such chelates would be beneficial. In accordance with this recognition, a hypoallergenic metal amino acid chelate composition can comprise metal amino acid chelates that are substantially free of allergens such that administration of the metal amino acid chelates in an effective amount to cause a medicinal or nutritional result in a subject does not produce a discernable adverse allergic reaction. The metal amino acid chelate composition can include chelates having a naturally occurring amino acid to metal molar ratio of from about 1:1 to 4:1.

In another embodiment, a hypoallergenic metal amino acid chelate-containing composition can comprise hypoallergenic metal amino acid chelates having a naturally occurring amino acid to metal molar ratio of from about 1:1 to 4:1, wherein the metal amino acid chelates are blended with one or more hypoallergenic formulation additive(s). The metal amino acid chelates and the formulation additive can be substantially free of allergens such that administration of the composition in an effective amount to cause a medicinal or nutritional result in a subject does not produce a discernable adverse allergic reaction.

In another embodiment, a method of preparing hypoallergenic metal amino acid chelates can comprise steps of a) selecting an amino acid source determined to be hypoallergenic; b) selecting a metal source determined to be hypoallergenic; and c) chelating an amino acid of the amino acid source to a metal of the metal source to form a hypoallergenic metal amino acid chelate. Optionally, hypoallergenic additives, including reagents for promoting the chelation process, can be added to the hypoallergenic metal amino acid chelates for formulation or finished product properties.

A method of administering metal amino acid chelates is also disclosed, and can comprise steps of a) identifying a subject susceptible to a type of allergic reaction; b) formulating a metal amino acid chelate; and c) administering the hypoallergenic amino acid to the subject. The formulating step can be carried out by i) selecting an amino acid source determined to be hypoallergenic with respect to the type of allergic reaction; ii) selecting a metal source determined to be hypoallergenic with respect to the type of allergic reaction, and iii) chelating an amino acid of the amino acid source to a metal of the metal source to form a hypoallergenic metal amino acid chelate. Optionally, hypoallergenic additives, including reagents for promoting the chelation process, can be added to the hypoallergenic metal amino acid chelates for formulation or finished product properties prior to or in conjunction with the administering step.

Additional features and advantages of the invention will be apparent from the following detailed description which illustrates, by way of example, features of the invention.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is to be noted that, as used in this specification and the appended claims, the singular forms "a," "an," and "the" include plural referents unless the context clearly dictates otherwise.

The term "substantially" is a term of magnitude. For example, when stating that a composition is "substantially free of allergens," what is meant is that allergens are not present to an extent that causes an allergic reaction in susceptible subjects.

The term "naturally occurring amino acid" or "traditional amino acid" shall mean amino acids that are known to be used for forming the basic constituents of proteins, including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. The term "naturally occurring" does not mean that the amino acid used in accordance with embodiments of the present invention is necessarily derived naturally, but that it can occur naturally, e.g., essential and non-essential amino acids.

The term "amino acid chelate(s)" or "metal amino acid chelate(s)" is intended to cover both the traditional definitions and the more modern definition of chelate as cited previously. Specifically, with respect to chelates that utilize traditional amino acid ligands, i.e. those used in forming proteins, chelate is meant to include metal ions bonded to amino acid ligands forming heterocyclic rings. Between the carboxyloxygen and the metal, the bond can be covalent or more ionic, but is preferably coordinate covalent. Additionally, at the α-amino group, the bond is typically a covalent or coordinate covalent bond.

When referring to "metal amino acid chelates" in the plural form, this phraseology does not necessarily infer that two distinct metal amino acid chelates are present. For example, a particulate batch of a single species of a metal amino acid chelate can be referred to as "metal amino acid chelates." Alternatively, the term "metal amino acid chelates" can also include multiple types of metal amino acid chelates in a batch, depending on the context.

The term "nutritionally relevant metal" is meant to include any polyvalent, e.g., divalent or trivalent, metal that can be used as part of a nutritional supplement, drug therapy, food fortificant, topical cosmetic, etc., that is known to be beneficial to animals including humans, and in some instances, plants. Nutritionally relevant metals are also known to be substantially non-toxic when administered in traditional amounts, as is known in the art. Examples of such metals include iron, zinc, copper, manganese, calcium, magnesium, chromium, vanadium, selenium, silicon, molybdenum, tin, nickel, boron, cobalt, gold, silver, and combinations thereof.

The term "hypoallergenic" refers to compositions where care has been taken in formulation and/or production to ensure minimal instance of allergic reactions in a target subject or class of subjects. Hypoallergenic can also refer to a composition that when contacted, e.g., topical, or ingested, e.g., food fortification or nutritional supplement, at customary levels to provide a nutritional, cosmetic, or medicinal effect, the contact or ingestion does not produce an adverse discernable allergic reaction to a target subject or class of subjects.

"Allergy" refers to an acquired and abnormal immune response to a substance or moiety of a substance (allergen) that produces an altered bodily reaction. Sensitization, or initial exposure to the allergen, precedes the allergic response, and subsequent contact with the allergen results in the altered bodily reactivity or response. An allergy can be an inherited or acquired trait.

The term "allergen" refers to a substance that causes manifestations of allergy, such as a protein or antigen. The FDA lists eight major allergen sources in the FDA Compliance Policy Guide, CPG 555.250, which includes: soy, peanuts, tree nuts (almonds, walnuts, etc.), crustaceans, fin fish, dairy, wheat, and eggs. Other known allergens that affect a relatively large percentage of the population may include corn, from which maltodextrin is derived, gelatin, whey, chocolate, strawberries, etc.

The term "subject" refers to a target warm-blooded animal to which hypoallergenic metal amino acid chelates or hypoallergenic metal amino acid chelate-containing compositions can be administered. In one embodiment, the subject or class of subjects can be human.

"Protein hypersensitivity" is a form of an allergy wherein an immune-mediated adverse reaction to the ingestion or contact with a protein or amino acid derived from that protein can occur.

Amino acids prepared by "synthetic" methods include chemical preparations that do not involve protein hydrolysis.

Amino acids prepared by "fermentation" methods typically include a bioprocess wherein an engineered or unengineered cell or organism produces the amino acids, usually on a relatively large scale.

With these definitions in mind, a hypoallergenic metal amino acid chelate composition can comprise metal amino acid chelates that are substantially free of allergens such that administration of the metal amino acid chelates in an effective amount to cause a medicinal, cosmetic, or nutritional result in a subject does not produce a discernable adverse allergic reaction. The metal amino acid chelate composition can include chelates having a naturally occurring amino acid to metal molar ratio of from about 1:1 to 4:1.

In another embodiment, a hypoallergenic metal amino acid chelate-containing composition can comprise hypoallergenic metal amino acid chelates having a naturally occurring amino acid to metal molar ratio of from about 1:1 to 4:1, wherein the metal amino acid chelates are blended with a hypoallergenic formulation additive, including hypoallergenic reagents. The metal amino acid chelates and the formulation additive can be substantially free of allergens such that administration of the composition in an effective amount to cause a medicinal, cosmetic, or nutritional result in a subject does not produce a discernable adverse allergic reaction.

In another embodiment, a method of preparing hypoallergenic metal amino acid chelates can comprise selecting an amino acid source determined to be hypoallergenic; selecting a metal source determined to be hypoallergenic; and chelating an amino acid of the amino acid source to a metal of the metal source to form a hypoallergenic metal amino acid chelate. In one embodiment, during the step of selecting the amino acid source, if the amino acid source is not hypoallergenic, alternative amino acid sources can be evaluated until a hypoallergenic amino acid source is ascertained. In another embodiment, during the step of selecting the metal source, if the metal source is not hypoallergenic, alternative metal sources can be evaluated until a hypoallergenic metal source is ascertained.

In another embodiment, a method of administering metal amino acid chelates is disclosed, and can comprise steps of identifying a subject susceptible to a type of allergic reaction, formulating a metal amino acid chelate, and administering the hypoallergenic amino acid to the subject. The formulating step can be carried out i) selecting an amino acid source determined to be hypoallergenic with respect to the type of allergic reaction; ii) selecting a metal source determined to be hypoallergenic with respect to the type of allergic reaction, and iii) chelating an amino acid of the amino acid source to a metal of the metal source to form a hypoallergenic metal amino acid chelate.

Determining whether a composition or its source is hypoallergenic indicates that some type of evaluative step be performed. For example, in determining whether an amino acid, including its source, as well as a metal source is hypoallergenic, an evaluation step can include steps such as reviewing literature or interviewing manufacturers associated with a product obtained from a third party, preparing the compositions or sources oneself to ensure that all components are hypoallergenic, and/or conducting an assay to verify that a composition is truly hypoallergenic.

Hypoallergenic Metal Amino Acid Chelates

In accordance with embodiments of the present invention, metal amino acid chelates that are hypoallergenic can be prepared by reacting hypoallergenic amino acids with hypoallergenic metal sources. As such, steps of preparing or selecting hypoallergenic amino acids as well as preparing or selecting hypoallergenic metal sources can be carried out to achieve this result.

Exemplary metals that can be used include iron, zinc, copper, calcium, magnesium, and/or manganese, which are common nutritional minerals used when supplementing the mineral balance of subjects, including humans. Further, trace metals, such as chromium, vanadium, selenium, silicon, molybdenum, tin, nickel, boron, cobalt, gold, and/or silver, or the like, can also be used. Regarding the metals that can be prepared or selected for use, metal sources that may include allergens can be avoided. For example, biological sources of metal may more likely include allergens that certain target subjects may be allergic to. Heme iron from hemoglobin, magnesium from chlorophyll, calcium from lactose, magnesium from magnesium stearate each exemplify metal sources that may be undesireable for use in certain circumstances. However, if such metal sources are processed such that allergens present are reduced to a level that is acceptable, or the use of the metal source would not be problematic with respect to a target subject class, then these metal sources may be acceptable for use. In other words, on a case by case basis, a metal source can be selected for use to meet the goals of the hypoallergenic composition to be formed. Examples of metal sources that typically do not include allergens include metal sulfates, metal carbonates, metal oxides, metal hydroxides, elemental metals, and the like.

Examples of amino acid sources that can be hypoallergenic include those not prepared by protein hydrolysis, those wherein the amino acid source is prepared by protein hydrolysis using a hypoallergenic protein, and amino acids that have been purified of allergens, such as by chromatography or bind-release separation technologies. The naturally occurring amino acids that can be used include alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof.

Specific examples of preferred metal amino acid chelates that can be used include embodiments wherein the amino acid to metal molar ratio is about 2:1, and wherein the metal is ferrous iron and the naturally occurring amino acid is glycine, the metal is copper and the naturally occurring amino acid is glycine, the metal is zinc and the naturally occurring amino acid is glycine, or the metal is manganese and the naturally occurring amino acid is glycine. Alternatively, the amino acid to metal molar ratio can be about 3:1, the metal can be ferric iron or chromium, and the naturally occurring amino acid can be glycine. In yet another embodiment, the amino acid to metal molar ratio can be about 1:1, the metal can be magnesium or calcium, and the naturally occurring amino acid can be glycine.

In each of the compositions and methods, the naturally occurring amino acid used to make the metal amino acid chelates may be provided by a production method other than protein hydrolysis, e.g., synthetic preparation or fermentation. Alternatively, if protein hydrolysis is used to provide the amino acid, then care can be taken to select or render the proteins hypoallergenic. For example, proteins derived from soy, peanuts, tree nuts, crustaceans, finfish, dairy, wheat, eggs, corn, gelatin, whey, chocolate, strawberries, etc., may be desirable to avoid, depending on the target subject class. Conversely, certain proteins derived from mammals, such as bovine or porcine protein, may be more generally acceptable for use across the spectrum of target subject classes. In still another embodiment, if the allergens are present due to residual proteins or peptides that may be present with the amino acid, then the allergens can be removed from the composition after formation of the metal amino acid chelates, such as by multiple washing steps, or by chromatography or non-chromatography bind-release separation methods.

There are many methods that can be used to ensure that a resulting metal amino acid chelate composition is hypoallergenic. For example, synthetic synthesis of amino acids can be used to provide hypoallergenic amino acids. In one embodiment, the synthesis of α-amino acids can be carried out by reaction of aldehydes with ammonia and hydrogen cyanide, followed by hydrolysis of the resulting α-aminonitriles. Amino acids prepared by this method are available from Dow Chemical and Chattem Chemicals, Inc., among others. Alternatively, amino acids can be prepared by the formation of azlactones by intramolecular condensation of acylglycines in the presence of acetic anhydride. The reaction of azlactones with carbonyl compounds followed by hydrolysis to the unsaturated α-acylamino acid and by reduction yields the amino acid. These synthetic methods of preparation are exemplary only, and are not intended to be limiting.

Fermentation can also be used to prepare amino acids that may be hypoallergenic. Amino acid fermentation is a method for producing amino acids using microorganisms to convert nutrients to amino acids. Specifically, raw materials, such as broths or syrups, can be added to microorganism culture media, and the microorganisms are allowed to produce the amino acids. For example, L-amino acids can be accumulated in a fermentation broth, from which they are subsequently isolated and purified. A common amino acid producer includes mutants of coryneform bacteria represented by the genera *Corynebacterium* and *Brevibacterium*. In addition to mutants of various types, obtained by mutation and selection (auxotrophic mutants, regulatory mutants, auxotrophic-regulatory mutants), the amino acid producers can be obtained by the methods of gene manipulation. The producers are able to synthesize amino acids from such carbon sources as sugar, ethanol, or methanol under optimal conditions of aeration. These conditions can be very different for the individual amino acids. Amino acids overproduction is influenced by the mechanisms of metabolic regulations (on the level of both activity and expression) and amino acid secretion (as diffusion and carrier-mediated membrane transport).

Other amino acid preparative process are described in part or in whole the following articles: *Determination of Amino Acids in Cell Cultures and Fermentation Broths*, Dionex Application Note 150, pp 1-15; *Production of Amino Acids by Analog-Resistant Mutants of Cyanobacterium Spirulina platenis*, Riccardi, G. et al., Journal of Bacteriology, pp. 102-107 (September 1981); *Cattle Nutrition—Mycotoxins* and *Intoxications*, various authors, Abstracts—XXII World Buiatrics Congress 2002, Hannover, Germany (Aug. 18-23, 2002—Abstract Nos. 1-364, 2-689, 3-229, 4-788, 5-755, 6-157, 7-825, 7-757, 9-226, 10-393, 11-645, 12-904, 13-802); *Lysine and other amino acids for feed: production and contribution to protein utilization in animal feeding*, Toride, Y. et al.; and *Acid-neutralizing activity during amino acid fermentation by Porphyromonas gingivalis, Prevotell intermedia and Fusobacterium nucleatum*, Takahashi, N. et al., Oral Microbiology Immunology, vol. 18, no. 2, 109-113 (5) (April 2003), each of which are incorporated herein by reference in their entireties.

In addition to synthetic and fermentation preparation methods, as well as certain proteolytic methods, there are other methods that can be used to render amino acids hypoallergenic. For example, U.S. Pat. No. 5,039,032, which is incorporated herein by reference, describes a method of preparing hypoallergenic protein from whey. Whey is typically recognized as a composition that many humans who are lactose intolerant are susceptible. In that patent, the protein is first hydrolyzed with a proteolytic enzyme and then the enzymatic hydrolyzate is subjected to a heat treatment to denature allergen-containing proteins which remain intact after the first hydrolysis. Then, the heated hydrolyzate is cooled, followed by further proteolytic enzyme hydrolysis to provide a hydrolyzate substantially free of allergens of protean origin. This hypoallergenic protein can then be hydrolyzed to form hypoallergenic amino acids to be used to form the hypoallergenic metal amino acid chelates in accordance with embodiments of the present invention.

Other methods used to denature protein to render it hypoallergenic include ultrafiltration to remove undesirable proteins or other materials. For example, U.S. Pat. No. 4,293,571, which is incorporated herein by reference, discloses a process for the purification of purified protein hydrolysate. In this process, an aqueous solution of protein is subjected to hydrolysis, and then is heat treated to denature the protein. The heat-treated material can then be ultrafiltered to eliminate protein.

Hypoallergenic Additives

Depending on the amount of a specific mineral to be administered in a metal amino acid chelate (or combination of minerals to be administered), hypoallergenic additives are typically formulated within a common composition with the metal amino acid chelates to provide desired properties that may not be inherently present in the metal amino acid chelate itself. As one embodiment of the present invention is drawn hypoallergenic metal amino acid chelate-containing compositions, care should be taken in selecting additives to administer with the metal amino acid chelates such that the composition, as a whole, is hypoallergenic.

Examples of formulation additives that can be admixed or co-administered with the metal amino acid chelates of the present invention include hypoallergenic organic acids, hypoallergenic free amino acids, hypoallergenic amino acid salts, hypoallergenic fillers, hypoallergenic flow control agents, hypoallergenic lubricants, hypoallergenic flow agents, hypoallergenic hydroscopicity minimizing agents, hypoallergenic pH control agents, hypoallergenic catalysts, hypoallergenic vitamins, hypoallergenic dust control agents, hypoallergenic binders, hypoallergenic disintegrating agents, hypoallergenic flavoring agents, hypoallergenic taste-reducing agents, hypoallergenic capsule shells, hypoallergenic shellacs, hypoallergenic waxes, hypoallergenic emulsifiers, hypoallergenic oils, combinations thereof, and other known additives that can be prepared to be hypoallergenic.

There are certain additives that can be formulated to be hypoallergenic, which can be included in amino-acid chelate-containing compositions that provide desired properties to the composition during formulation or to the finished composition. For example, maltodextrin can be added as a filler and a flow agent. Additionally, maltodextrin can help to reduce the hydroscopicity of the composition as a whole. Grain flours, such as rice flour or wheat flour, can also be added as a filler, as well as vegetable flours or powders, such as soy flour. In another embodiment, a filler that can be added is inulin, such as hypoallergenic low fiber inulin derived from chicary. Fumed silica, stearic acids, and/or talc can also be added as a flow controlling agents. When including a flow control agent or filler, as described above, care should be taken to select or prepare the additive such that it meets target subject allergic criteria, e.g., will not illicit an allergic reaction. For example, if a class of subjects is believed to be allergic to corn (maize), then corn-derived maltodextrin may be undesirable for use.

In addition to the flow agents and fillers, other compositions that can be added include organic acids. Citric acid, fumaric acid, succinic acid, tartaric acid, malic acid, lactic acid, gluconic acid, ascorbic acid, pantothenic acid, folic acid, lipoic acid, oxalic acid, maleic acid, formic acid, acetic acid, pyruvic acid, adipic acid, and alpha-ketoglutaric acid are each exemplary of such organic acids, though others can also be used. Free amino acids or amino acid salts can also be present in the composition. Additionally, mineral oils for dust control, binders for tableting (carboxymethyl cellulose, ethyl cellulose, glycerol, etc.), flavoring agents or taste-free additives for organoleptic properties, or the like can also be included.

Other classes of formulation additives that can be included with the hypoallergenic metal amino acid chelates are vitamins, coenzymes, cofactors, herbs or herbal extracts, protein powders, or the like. Hypoallergenic vitamins that can be used include Vitamin A, the Vitamin B group of vitamins, e.g., folic acid, Vitamin $B_1$, Vitamin $B_2$, Vitamin $B_3$, Vitamin $B_5$, Vitamin $B_6$, or Vitamin $B_{12}$, Vitamin C, Vitamin D, Vitamin E, and the like. Coenzymes can also be used, which are organic compounds that combine with apoenzymes to form active enzymes. Cofactors that can be present include coenzymes and metals that are required for an enzyme to be active, some of which can be provided by the metal amino acid chelate itself.

In each of the embodiments described herein, the compositions can be in the form of tablets, capsules, powders, crystals, granules, liquids, or the like. Shellacs or waxes can be used as tablet coatings, provided they are hypoallergenic to the class of subjects being targeted. Likewise, if using capsules to deliver a composition in accordance with embodiments of the present invention, the encapsulating material should also be hypoallergenic. For example, the encapsulating material can be of vegetable sterols or gelatin, for example, provided the encapsulating material is hypoallergenic to the class of subjects that the composition is to be delivered, e.g., bovine or porcine gelatin can often be desirable for use. Regarding liquids, compositions can also be included in liquid formulations that act to main the solubility of the metal amino acid chelate and/or other additives that may be present. For example, U.S. Pat. No. 6,716,814, which is incorporated herein by reference in its entirety, describes a method enhancing the solubility of iron amino acid chelates and iron proteinates. Such methods and solubility enhancing compositions can be used, provided the compositions used are hypoallergenic.

EXAMPLES

The following examples are illustrative of a present hypoallergenic metal amino acid chelates and metal amino acid chelate-containing formulations. As such, the following examples should not be considered as limitations of the present invention, but merely demonstrate the effectiveness of the methods and compositions described herein.

Example 1

To about 700 ml of deionized water containing 50 g citric acid is added 225 g of a synthetically produced glycine to form a clear solution. The synthetic production method for preparing the glycine is by reacting aldehydes with ammonia and hydrogen cyanide, followed by hydrolysis of the resulting α-aminonitriles. To this solution, 55.8 g of elemental iron substantially free of allergens is slowly added. The solution is heated at about 50° C. for 48 hours, or until all the iron is observed to go into solution. The product is cooled, filtered, and spray dried yielding an iron triglycine amino acid chelate. All of the compositional components used in the preparation are hypoallergenic, and none of the equipment selected for use should affect the hypoallergenic nature of the chelates.

Example 2

A solution is prepared including 10.1 parts by weight of fermentation-produced glycine dissolved in 82.2 parts by weight water. To this solution is added 4.4 parts by weight zinc oxide. The molar ratio of glycine to zinc is 2:1. The reaction mixture is allowed to stand for about 14 hours and turned an opalescent color. After standing, the mixture is heated to about 70° C. and spray dried to obtain a zinc bisglycinate amino acid chelate powder having a melting point of about 209° C. which turned red upon melting. The zinc content of the chelate is about 20 wt %. The dried product has a moisture content of about 7 wt %, and when reconstituted in water, has a pH of about 8.0. All of the compositional components used in the preparation are hypoallergenic, and none of the equipment selected for use should affect the hypoallergenic nature of the chelates.

Example 3

A copper carbonate solution is prepared by adding 6.1 parts by weight of hypoallergenic cupric carbonate to 80.9 parts by weight water. This solution is allowed to stand without agitation for about two hours. To this solution is added 8.2 parts by weight of a synthetically prepared glycine, and the mixture is slowly stirred for about two more hours. A hazy blue solution is observed. The synthetic production method for preparing the glycine is by reacting aldehydes with ammonia and hydrogen cyanide, followed by hydrolysis of the resulting α-aminonitriles. To the hazy blue solution is added 65 parts by weight of a 15 wt % citric acid solution and the mixture is stirred until a clear blue solution is observed. This solution is spray dried resulting in a copper bisglycinate powder having a copper content of about 14 wt % and which melts at about 194° C. Upon being reconstituted in water, the pH of the resulting solution is about 7.5. All of the compositional components used in the preparation are hypoallergenic, and none of the equipment selected for use should affect the hypoallergenic nature of the chelates.

Example 4

A mixture of 42.93 grams of zinc sulfate, 12 grams of methionine, and 30 grams of glycine are reacted in an aqueous environment for 60 minutes at a temperature of about 65 to 70° C. The glycine and methionine are prepared using synthetic processes. Specifically, the synthetic production method for preparing the glycine and methionine is by reacting aldehydes with ammonia and hydrogen cyanide, followed by hydrolysis of the resulting α-aminonitriles. The reaction of the zinc sulfate, methionine, and glycine produces a zinc amino acid chelate having a ligand component to metal molar ratio of about 2:1, a theoretical average zinc content of about 26.8% by weight, and a glycine to methionine molar ratio of about 5:2. Due to the presence of the sulfate anion, the actual average zinc weight percentage is about 18.2%. All of the compositional components used in the preparation are hypoallergenic, and none of the equipment selected for use should affect the hypoallergenic nature of the chelates.

Example 5

Into about 1300 grams of water is dissolved 210.72 grams of a synthetic glycine and 79.86 grams of calcium oxide. The synthetic production method for preparing the glycine is by reacting aldehydes with ammonia and hydrogen cyanide, followed by hydrolysis of the resulting α-aminonitriles. The solution of calcium oxide and glycine is stirred until all of the calcium oxide appeared to be fully dissolved, i.e. about 15 minutes. The resulting reaction forms a calcium bisglycinate chelate or complex solution. Next, to the calcium bisglycinate chelate or complex solution is added 381.55 grams of ferrous sulfate hydrate containing 20% ferrous iron by weight. Again, the solution is constantly stirred while the ferrous sulfate dissolves and a white precipitate of calcium sulfate forms. About 287 grams of a ferrous glycine chelate is formed having a ligand to metal molar ratio of about 2:1. All of the compositional components used in the preparation are hypoallergenic, and none of the equipment selected for use should affect the hypoallergenic nature of the chelates.

Example 6

About 2252 grams of water is used to dissolve 450.42 grams of fermentation-produced glycine and 168.24 grams of calcium oxide into solution. The resulting reaction formed a calcium trisglycinate chelate or complex solution. Next, 500.18 grams of chromic sulfate hydrate containing 19 wt % chromium is added to the calcium chelate solution. The solution is stirred while the copper sulfate is dissolved and as a white precipitate of calcium sulfate formed. Upon completion of the reaction, about 545 grams of a chromic trisglycinate chelate having a ligand to metal molar ratio of about 3:1 is formed. All of the compositional components used in the preparation are hypoallergenic, and none of the equipment selected for use should affect the hypoallergenic nature of the chelates.

Example 7

Into about 923 grams of water is dissolved 150.14 grams of synthetic glycine. The synthetic production method for preparing the glycine is by reacting aldehydes with ammonia and hydrogen cyanide, followed by hydrolysis of the resulting α-aminonitriles. Next, 57.25 grams of calcium oxide, which is about 70 wt % calcium, is added. The solution is continually stirred until all of the calcium oxide is dissolved. This takes about 15 minutes. No heat is applied for this particular reaction. The resulting reaction forms a calcium bisglycinate chelate or complex and water. Next, 254.18 grams of copper sulfate hydrate containing 25% copper by weight is added to the calcium chelate solution. Again, the solution is constantly stirred while the copper sulfate is dissolved. As the copper sulfate goes into solution, a white precipitate of calcium sulfate is formed. Upon completion of the reaction, about 214 grams of a copper glycine chelate having a ligand to metal molar ratio of 2:1 is formed. All of the compositional components used in the preparation are hypoallergenic, and none of the equipment selected for use should affect the hypoallergenic nature of the chelates.

Example 8

About 250 grams of fermentation-produced glycine is dissolved into 937.8 grams of water. Once the glycine is significantly dissolved, about 95 grams of calcium oxide is added. The solution is continually stirred for about 15 minutes until all of the calcium is dissolved. The resulting reaction forms a calcium bisglycinate chelate or complex and water. Next, 299.97 grams of zinc sulfate hydrate containing 35% zinc by weight is added to the calcium chelate solution. Upon constant stirring, the zinc sulfate goes into solution and a white precipitate of calcium sulfate is formed. About 355 grams of a zinc glycine chelate having a ligand to metal molar ratio of about 2:1 is also formed. All of the compositional components used in the preparation are hypoallergenic, and none of the equipment selected for use should affect the hypoallergenic nature of the chelates.

Example 9

An open electrolytic cell is constructed consisting of an anode compartment and a cathode compartment divided by a cation permselective membrane. The anode is pure copper metal, providing the metal to form the chelate at the appropriate time. The volume of the anode compartment is approximately 400 cc and the volume of the cathode compartment is about 650 cc. A transformer and rectifier system is utilized to apply a direct current voltage across the cell. The anolyte solution includes a synthetically produced aqueous glycine having a glycine concentration of about 20%, which is circulated continuously throughout the cell compartment and past the anode. The synthetic production method for preparing the glycine is by reacting aldehydes with ammonia and hydrogen cyanide, followed by hydrolysis of the resulting α-aminonitriles. The catholyte solution is a 1 wt % citric acid solution. The initial temperature of the analyte and catholyte solutions is about 40° C. The applied voltage to the transformer is 75 V A.C. The initial voltage across the cell is 5 V D.C. at an amperage of 27 amps. The temperature within each compartment rises quite rapidly and levels off at about 90° C. in the anode compartment and 94° C. in the cathode compartment. The amperage slowly increases to about 34 amps and then remains constant and the voltage across the cell decreases slowly during the entire hour of operation from 5 V D.C. to 2.2 V D.C. Upon cooling to room temperature, a blue precipitate is formed and separates from the anolyte solution. Upon assay, the blue precipitate is shown to be a copper glycine chelate containing 6% copper and having a ligand to copper ration of 2:1. The resulting chelate precipitate is free of any anions. The current flow between the anode and cathode compartments is made possible by the migration of hydrogen ions through the cation permselective membrane. Also, upon cooling it is found that certain of the copper ions had also migrated through the membrane and are loosely plated on the cathode. All of the compositional components used in the preparation are hypoallergenic, and none of the equipment selected for use affected the hypoallergenic nature of the prepared chelates.

Example 10

The metal amino acid chelate prepared in accordance with Example 1 is spray dried and blended with hypoallergenic fumed silica (about 0.1 wt % to 5 wt % of composition) and hypoallergenic maltodextrin (about 0.1 wt % to 85 wt % of composition). A free flowing powder having acceptable hydroscopicity is formed.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method of preparing a hypoallergenic metal amino acid chelate composition, comprising:
   a) selecting an amino acid source determined to be hypoallergenic;
   b) selecting a metal source determined to be hypoallergenic; and
   c) chelating an amino acid of the amino acid source to a metal of the metal source to form a hypoallergenic metal amino acid chelate composition wherein the hypoallergenic metal amino acid chelate composition includes coordinate covalent bonding and has an amino acid to metal ratio from about 1:1 to 3:1.

2. A method as in claim 1, wherein during the step of selecting the amino acid source, if a first amino acid source is not hypoallergenic, additional amino acid sources are evaluated until a hypoallergenic amino acid source is ascertained.

3. A method as in claim 1, wherein during the step of selecting the metal source, if a first metal source is not hypoallergenic, additional metal sources are evaluated until a hypoallergenic metal source is ascertained.

4. A method as in claim 1, wherein the amino acid source is rendered hypoallergenic after formation, but before chelation with the metal.

5. A method as in claim 1, further comprising selecting an additive determined to be hypoallergenic, and including the additive as a mixture with the hypoallergenic metal amino acid chelate.

6. A method as in claim 5, wherein the additive is selected from the group consisting of hypoallergenic organic acids, hypoallergenic free amino acids, hypoallergenic amino acid salts, hypoallergenic fillers, hypoallergenic flow control agents, hypoallergenic lubricants, hypoallergenic flow agents, hypoallergenic hydroscopicity reducing agents, hypoallergenic pH control agents, hypoallergenic catalysts, hypoallergenic vitamins, hypoallergenic dust control agents, hypoallergenic binders, hypoallergenic disintegrating agents, hypoallergenic flavoring agents, hypoallergenic flavoring agents, hypoallergenic taste-reducing agents, hypoallergenic capsule shells, hypoallergenic shellacs, hypoallergenic waxes, hypoallergenic gelatin sources, hypoallergenic emulsifiers, hypoallergenic oils, and combinations thereof 7. A method as in claim 5, wherein the additive is a hypoallergenic organic acid selected from the group consisting of citric acid, fumaric acid, succinic acid, tartaric acid, malic acid, lactic acid, gluconic acid, ascorbic acid, pantothenic acid, folic acid, lipoic acid, oxalic acid, maleic acid, formic acid, acetic acid, pyruvic acid, adipic acid, alpha-ketoglutaric acid, and mixtures thereof.

8. A method as in claim 5, wherein the additive is a hypoallergenic filler selected from the group consisting of grain flours, maltodextrins, vegetable flours or powders, inulin, and combinations thereof.

9. A method as in claim 5, wherein the additive is a hypoallergenic flow control agent selected from the group consisting of fumed silica, steuric acid, talc, and combinations thereof.

10. A method as in claim 5, wherein the additive is selected from the group consisting of hypoallergenic free amino acids, hypoallergenic amino acid salts, and combinations thereof.

11. A method as in claim 5, wherein the additive is selected from the group consisting of vitamins, coenzymes, cofactors, herbs, herbal extracts, protein powders, and combinations thereof.

12. A method as in claim 5, wherein the additive is selected from the group consisting of mineral oils, binders, flavoring or taste-free additives, and combinations thereof.

13. A method as in claim 1, wherein the naturally occurring amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof.

14. A method as in claim 1, wherein the metal is selected from the group consisting of iron, zinc, copper, manganese, calcium, chromium, vanadium, selenium, silicon, molybdenum, tin, nickel, boron, cobalt, gold, silver, and combinations thereof.

15. A method as in claim 1, wherein the metal is ferrous iron and the naturally occurring amino acid is glycine, and wherein the glycine to iron molar ratio is about 2:1.

16. A method as in claim 1, wherein the metal is copper and the naturally occurring amino acid is glycine, and wherein the glycine to copper molar ratio is about 2:1.

17. A method as in claim 1, wherein the metal is zinc and the naturally occurring amino acid is glycine, and wherein the glycine to zinc molar ratio is about 2:1.

18. A method as in claim 1, wherein the metal is manganese and the naturally occurring amino acid is glycine, and wherein the glycine to manganese molar ratio is about 2:1.

19. A method as in claim 1, wherein the metal is ferric iron and the naturally occurring amino acid is glycine, and wherein the glycine to ferric iron molar ratio is about 3:1.

20. A method as in claim 1, wherein the metal is chromium and the naturally occurring amino acid is glycine, and wherein the glycine to chromium molar ratio is about 3:1.

21. A method as in claim 1, wherein the metal is magnesium and the naturally occurring amino acid is glycine, and wherein the magnesium to glycine molar ratio is about 1:1.

22. A method as in claim 1, wherein the metal is calcium and the naturally occurring amino acid is glycine, and wherein the calcium to glycine molar ratio is about 1:1.

23. A method as in claim 22, wherein the allergens are removed from the naturally occurring amino acid after formation, but before chelation with the metal.

24. A method as in claim 22, wherein the subject is human.

25. A method as in claim 1, wherein the hypoallergenic metal amino acid chelate composition is substantially free of allergens such that upon administration of the composition to a subject in an effective Mount to cause a medicinal or nutritional result, the composition does not produce a discernable adverse allergic reaction in the subject.

26. A method as in claim 1, wherein the amino acid source is prepared by synthetic synthesis.

27. A method as in claim 1, wherein the amino acid source is prepared by fermentation.

28. A method of administering a metal amino acid chelate composition, comprising:
   a) identifying a subject susceptible to a type of allergic reaction;
   b) formulating a metal amino acid chelate by:
      i) selecting an amino acid source determined to be hypoallergenic with respect to the type of allergic reaction;
      ii) selecting a metal source determined to be hypoallergenic with respect to the type of allergic reaction, and
      iii) chelating an amino acid of the amino acid source to a metal of the metal source to form a hypoallergenic metal amino acid chelate composition; and
   c) administering the hypoallergenic metal amino acid composition to the subject wherein the hypoallergenic metal amino acid chelate composition includes coordinate covalent bonding and has an amino acid to metal ratio from about 1:1 to 3:1.

29. A method as in claim 28, wherein the subject is allergic to at least one of soy, peanuts, tree nuts, crustaceans, finfish, dairy, wheat, eggs, corn, gelatin, whey, chocolate, and strawberries.

30. A method as in claim 28, wherein during the step of selecting the amino acid source, if a first amino acid source is not hypoallergenic, additional amino acid sources are evaluated until a hypoallergenic amino acid source is ascertained.

31. A method as in claim 30, wherein during the step of selecting the metal source, if a first metal source is not hypoallergenic, additional metal sources are evaluated until a hypoallergenic metal source is ascertained.

32. A method as in claim 28, wherein the amino acid source is rendered hypoallergenic after formation, but before chelation with the metal.

33. A method as in claim 28, further comprising steps of selecting an additive determined to be hypoallergenic, and including the additive as a mixture with the hypoallergenic metal amino acid chelate.

34. A method as in claim 33, wherein the additive is selected from the group consisting of hypoallergenic organic acids, hypoallergenic free amino acids, hypoallergenic amino acid salts, hypoallergenic fillers, hypoallergenic flow control agents, hypoallergenic lubricants, hypoallergenic flow agents, hypoallergenic hydroscopicity reducing agents, hypoallergenic pH control agents, hypoallergenic catalysts, hypoallergenic vitamins, hypoallergenic dust control agents, hypoallergenic binders, hypoallergenic disintegrating agents, hypoallergenic flavoring agents, hypoallergenic flavoring agents, hypoallergenic taste-reducing agents, hypoallergenic capsule shells, hypoallergenic shellacs, hypoallergenic waxes, hypoallergenic gelatin sources, hypoallergenic emulsifiers, hypoallergenic oils, and combinations thereof.

35. A method as in claim 33, wherein the additive is an hypoallergenic organic acid selected from the group consisting of citric acid, fumaric acid, succinic acid, tartaric acid, malic acid, lactic acid, gluconic acid, ascorbic acid, pantothenic acid, folic acid, lipoic acid, oxalic acid, maleic acid, formic acid, acetic acid, pyruvic acid, adipic acid, alplia-ketoglutaric acid, and mixtures thereof.

36. A method as in claim 33, wherein the additive is a hypoallergenic filler selected from the group consisting of grain flours, maltodextrins, vegetable flours or powders, inulin, and combinations thereof.

37. A method as in claim 33, wherein the additive is a hypoallergenic flow control agent selected from the group consisting of filmed silica, stearic acid, talc, and combinations thereof.

38. A method as in claim 33, wherein the additive is selected from the group consisting of hypoallergenic free amino acids, hypoallergenic amino acid salts, and combinations thereof.

39. A method as in claim 33, wherein the additive is selected from the group consisting of vitamins, coenzymes, cofactors, herbs, herbal extracts, protein powders, and combinations thereof.

40. A method as in claim 33, wherein the additive is selected from the group consisting of mineral oils, binders, flavoring or taste-free additives, and combinations thereof.

41. A method as in claim 28, wherein the naturally occurring amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, praline, serine, threonine, tryptophan, tyrosine, valine, and combinations thereof.

42. A method as in claim 28, wherein the metal is selected from the group consisting of iron, zinc, copper, manganese, calcium, chromium, vanadium, selenium, silicon, molybdenum, tin, nickel, boron, cobalt, gold, silver, and combinations thereof.

43. A method as in claim 28, wherein the metal is ferrous iron and the naturally occurring amino acid is glycine, and wherein the glycine to iron molar ratio is about 2:1.

44. A method as in claim 28, wherein the metal is copper and the naturally occurring amino acid is glycine, and wherein the glycine to copper molar ratio is about 2:1.

45. A method as in claim 28, wherein the metal is zinc and the naturally occurring amino acid is glycine, and wherein the glycine to zinc molar ratio is about 2:1.

46. A method as in claim 28, wherein the metal is manganese and the naturally occurring amino acid is glycine, and wherein the glycine to manganese molar ratio is about 2:1.

47. A method as in claim 28, wherein the metal is ferric iron and the naturally occurring amino acid is glycine, and wherein the glycine to ferric iron molar ratio is about 3:1.

48. A method as in claim 28, wherein the metal is chromium and the naturally occurring amino acid is glycine, and wherein the glycine to chromium molar ratio is about 3:1.

49. A method us in claim 28, wherein the metal is magnesium and the naturally occurring amino acid is glycine, and wherein the magnesium to glycine molar ratio is about 1:1.

50. A method as in claim 28, wherein the metal is calcium and the naturally occurring amino acid is glycine, and wherein the calcium to glycine molar ratio is about 1:1.

51. A method as in claim 28, wherein the hypoallergenic metal amino acid chelate composition is substantially free of allergens such that upon administration of the composition to the subject in an effective amount to cause a medicinal or nutritional result, the composition does not produce a discernable adverse allergic reaction in the subject.

52. A method as in claim 51, wherein the allergens are removed from the naturally occurring amino acid after formation, but before chelation with the metal.

53. A method as in claim 28, wherein the subject is human.

54. A method as in claim 28, wherein the amino acid source is prepared by synthetic synthesis.

55. A method as in claim 28, wherein the amino acid source is prepared by fermentation.

* * * * *